United States Patent
Krantz et al.

(10) Patent No.: US 6,646,281 B1
(45) Date of Patent: Nov. 11, 2003

(54) DIFFERENTIAL DETECTOR COUPLED WITH DEFOCUS FOR IMPROVED PHASE DEFECT SENSITIVITY

(75) Inventors: Matthias C. Krantz, Altenholz (DE); Donald W. Pettibone, San Jose, CA (US); Damon F. Kvamme, San Jose, CA (US); Stan Stokowski, Danville, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 10/094,305

(22) Filed: Mar. 7, 2002

Related U.S. Application Data

(60) Provisional application No. 60/344,225, filed on Dec. 28, 2001.

(51) Int. Cl.[7] .................................................. G01B 9/02
(52) U.S. Cl. ................... 250/559.45; 348/125
(58) Field of Search .............. 250/548, 559.45, 250/559.46; 348/125, 126, 128; 356/399–401, 237.1–237.5, 394; 382/144

(56) References Cited

U.S. PATENT DOCUMENTS

| | | | | |
|---|---|---|---|---|
| 5,430,548 A | * | 7/1995 | Hiroi et al. | 250/548 |
| 6,134,014 A | * | 10/2000 | Tzu et al. | 356/239.2 |
| 6,327,033 B1 | * | 12/2001 | Ferguson et al. | 356/394 |
| 2001/0019625 A1 | * | 9/2001 | Kenan et al. | 382/144 |

* cited by examiner

Primary Examiner—Stephone B. Allen
(74) Attorney, Agent, or Firm—Beyer Weaver & Thomas, LLP

(57) ABSTRACT

Provided are apparatus and methods for detecting phase defects. The invention relies generally on the distortion of light as it passes through defects in phase shift masks to detect these defects. Light traveling through a defect, such as a bump in an etched area will travel at a different rate than light traveling through air. In order to enhance the signals generated from the defects, the invention in several embodiments provides a defocused light inspection beam by setting the focus of the beam to a level above or below the photomask subject to inspection. The light from the photomask is collected by a detector split into at least two portions, each generating a signal. A resulting differential signal produced from the signals generated at each of the two detector portions is used to determine whether a defect in the photomask is present, in one embodiment, by generating an image from the resulting signal.

39 Claims, 6 Drawing Sheets

Schematic Layout of Zernike Phase Contrast Microscope

DIFFERENTIAL DETECTOR COUPLED WITH DEFOCUS FOR IMPROVED PHASE DEFECT SENSITIVITY

CROSS-REFERENCE TO RELATED APPLICATION

This application takes priority under U.S.C. 119(e) of U.S. Provisional Application No.: 60/344,225 filed Dec. 28, 2001 entitled, "DIFFERENTIAL DETECTOR COUPLED WITH DEFOCUS FOR IMPROVED PHASE DEFECT SENSITIVITY" by Matthias C. Krantz, Donald W. Pettibone, Damon F. Kvamme and Stan Stokowski, which is incorporated by reference in its entirety for all purposes.

BACKGROUND OF THE INVENTION

The present invention relates to methods and apparatus for detecting defects in masks used in semiconductor processing. More particularly, the present invention relates to apparatus and methods for detecting defects in phase shift masks.

Fabrication of semiconductor wafers typically relies on photolithography to produce circuit patterns on layers of a wafer. The wafer is coated with a "photoresist". Light is then transmitted through the mask and imaged onto the wafer. Photoresist is a material which is sensitive to light. A negative photoresist cures or hardens when exposed to light, so that the unexposed areas can be washed away. For example, in one system, ultraviolet light is used to expose a portion of the photoresist layer. A positive photoresist reacts in the opposite manner, the exposed regions can be washed away. The photoresist that is left acts as a mask, so that materials may be deposited in the areas not covered by photoresist to thereby form patterns on the wafer. The photoresist is then removed.

Designers and manufacturers constantly strive to develop smaller devices from the wafers, recognizing that circuits with smaller features generally have greater speeds and increased yield (numbers of usable chips produced from a standard semiconductor wafer). Photolithography equipment manufacturers have generally employed equipment using progressively smaller wavelengths to a current size below 193 nm in order to achieve smaller feature sizes. However, as the size of the circuit features decrease, physical limits such as the convergence between the wavelength of the light used to create the photoresist mask and the wafer feature sizes present obstacles to further reduction in feature size using the same semiconductor fabrication equipment.

Designers of such equipment have discovered that a phase shift mask (PSM) will allow the patterning of smaller features, even as the feature size approaches the wavelengths of the light used to create the photoresist pattern from the PSM. In some cases the use of a PSM may decrease the minimum feature size by a factor of two. With PSM, the mask no longer looks like the design shapes. Instead, the PSM contains shapes which cause the design shapes to appear as a result of constructive and destructive interference of light passing through the PSM. Alternating phase shift masks generally use an etching technique to etch a small depression into the mask. Light passing through the depression experiences a phase shift relative to the unetched areas, creating sharper images at the wafer. While the overall process uses particular design rules for minimum feature size, a PSM allows circuits with more aggressive critical dimensions to be consistently built using existing lithography tools.

Due to their importance in decreasing feature size while using existing equipment, semiconductor and semiconductor equipment manufacturers are highly motivated to detect PSM defects. Given the small size of the features and the volumes of wafers to be produced from a mask, it is essential that defects be detected in the masks to either enable repairs, where appropriate, of the mask or discard unsalvageable masks prior to production.

Conventional inspection techniques such as optical methods work well in identifying defects of typical chrome on glass masks. These defects include the placement of chrome in unintended places and the absence of chrome portions where desired. A conventional chrome on glass mask is shown in FIGS. 1A and 1B. FIG. 1A shows a cross section with chrome sections 102 and 104 deposited on transparent layer 106. A typical material for layer 106 is quartz, due to its ability to transmit light. FIG. 1B is a top view of the photomask showing a typical defect 108. Conventional optical inspection techniques work well in identifying such defects because the amplitude of the light transmitted through the defect is directly affected, i.e., the absence of the normally opaque chrome section allows light to be transmitted and detected in a location where such detection is unexpected. Contaminants on the glass can be identified by using either transmitted or reflected light or a combination of the two. The defects directly affect the amplitude of light passing through and reflected from the mask and are amenable to measurement by the above referenced conventional techniques.

Phase shift defects, however, present unusual problems. Imaging of phase objects and detection of phase defects typically requires special imaging methods to convert the phase information into intensity differences at the imaging detector. Numerous methods have been proposed to accomplish this including the Zernike phase contrast, differential interference contrast (DIC), differential phase contrast (DPC), defocused imaging, and interferometric techniques. Most of these methods involve changing the phase delay of the optical wavefront in the pupil plane of the imaging system in a way that will produce the greatest intensity effect at the detector for a given phase defect or phase object. The optimum method greatly depends on the phase shifts present in the object. In biological samples weak phase shifts need to be imaged. In phase shift masks for photolithography strong phase shifters are used. As a result, a sensitive defect detection system for phase defects on phase shift masks must detect weak phase objects in the presence of strong phase and amplitude objects. Of particular interest in the design is the response of a system to phase edges. Another important aspect for automated photomask inspection systems is whether the system response to phase objects is isotropic in the plane of the object. An anisotropic response as yielded by the DIC or a Nomarski technique or the linear DPC technique may be acceptable for visual inspection but complicates automated inspection.

For the foregoing reasons, there is a need for improved methods and apparatus capable of detecting phase shift mask defects in the presence of both weak and strong phase shifts.

SUMMARY OF THE INVENTION

To achieve the foregoing, the present invention provides apparatus and methods for detecting phase defects.

The invention relies generally on scanner type imaging systems and detects phase defects on photomasks by their modification of the light passing through the mask. Much of the detail provided in the specification for practicing the invention is given for scanners. Those skilled in the art, having the benefit of the details provided in this specification, will appreciate that the invention may also be implemented on projector type imaging systems. Specifically, the invention relies on the modification of the phase of the wavefront at the pupil plane of the optical imaging system using defocus in conjunction with the differential detection of the image intensity from different segments of a detector.

In order to enhance the signals generated from phase defects, the invention in several embodiments provides a defocused light inspection beam by setting the focus of the scanning beam to a level above or below the photomask subject to inspection, resulting in a defocused beam. The light from the scanning beam reflected or transmitted by the photomask is collected by a detector split into at least two portions, each generating a signal. The detector is typically positioned at or near the pupil plane. A resulting differential signal produced from the signals generated at each of the two detector portions is used to determine whether a defect in the photomask is present, in one embodiment, by generating an image from the resulting signal.

In one aspect, the first portion of the detector is a circular region and the second portion is an annular region outside the first region.

In one aspect the invention provides a method for detecting phase defects in a semiconductor processing photomask by using a complex amplitude plate such as a Zernike phase shift plate or similar phase plate. The beam generated using a Zernike phase plate or similar phase plate is used to derive a differential signal from the two portions of the detector to produce the resulting signal indicating whether phase defects are present.

In another aspect the invention provides a method of detecting phase defects in a first mode using a defocused light beam and a differential signal from the two portions of the detector. In a second mode, detecting pattern defects occurs by adjusting the focus of the optical inspection beam to the surface of the photomask and by summing the signals from the first and second portions of the detector to generate the resulting signal to produce at-focus, normal imaging for Cr defects.

These and other features and advantages of the present invention are described below with reference to the drawings.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 2A:
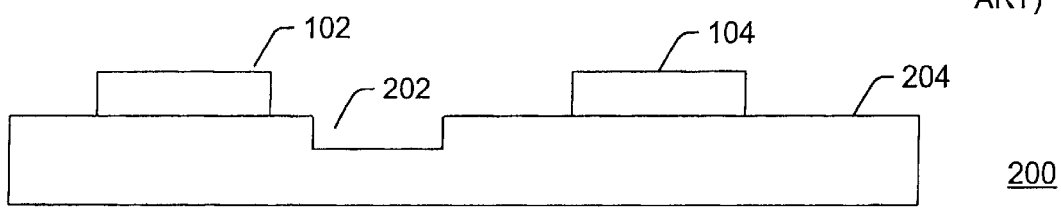
FIGS. 2A and 2B depict a cross section of a photomask with etched phase shift sections.
Figure 2B:
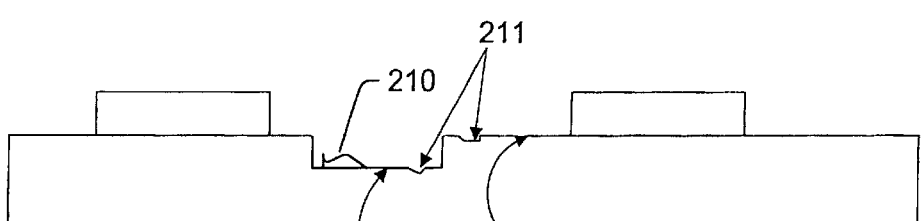

Several embodiments of the present invention rely on the phase shifting caused by defects to detect their presence in a phase shift mask. Phase shift masks change the phase of the light waves travelling through the mask to expose the photoresist layer on the semiconductor wafer. The phase shifting (e.g., by 180 degrees) causes cancellation in particular portions of the light passing through the mask, thus allowing the printing of smaller features. FIG. 2A is a cross section of an alternating phase shift mask 200. The phase shift results from the etched portion 202 of the quartz mask material 204. Light transmitted through the etched portion experiences an advanced phase shift relative to light transmitted through the unetched portions of mask material 204. A typical etch depth for etch portion 202 is about one wavelength to produce a 180 degree phase shift in a mask with refractive index of 1.5, i.e. about 250 nm. Example defects can include a bump (e.g., 210 shown in FIG. 2B), when the etch does not proceed to the full depth in one or more areas, and a divot (e.g., 211), which may be located on both the etched surface 212 and unetched surface 214. The detection techniques of the present invention take advantage of the diffraction of the incident field when travelling through defects such as bumps 210 or divots 211.

The invention relies generally on scanner type imaging systems and detects phase defects on photomasks by their modification of the light passing through the mask. Much of the detail provided in the specification for practicing the invention is given for scanners. Those skilled in the art, having the benefit of the details provided in this specification, will appreciate that the invention may also be implemented on projector type imaging systems. Specifically, the invention relies on the modification of the phase of the wavefront at the pupil plane of the optical imaging system using defocus in conjunction with the differential detection of the image intensity from different segments of a detector in the detector plane. In a conventional imaging microscope the equivalent step to having a segmented detector would be to have a segmented illumination source, which would then require either multiple passes with different illumination sectors or use of some other technique, relying on polarization for instance, to be able to separate the images obtained from different illumination sectors.

Figure 3:
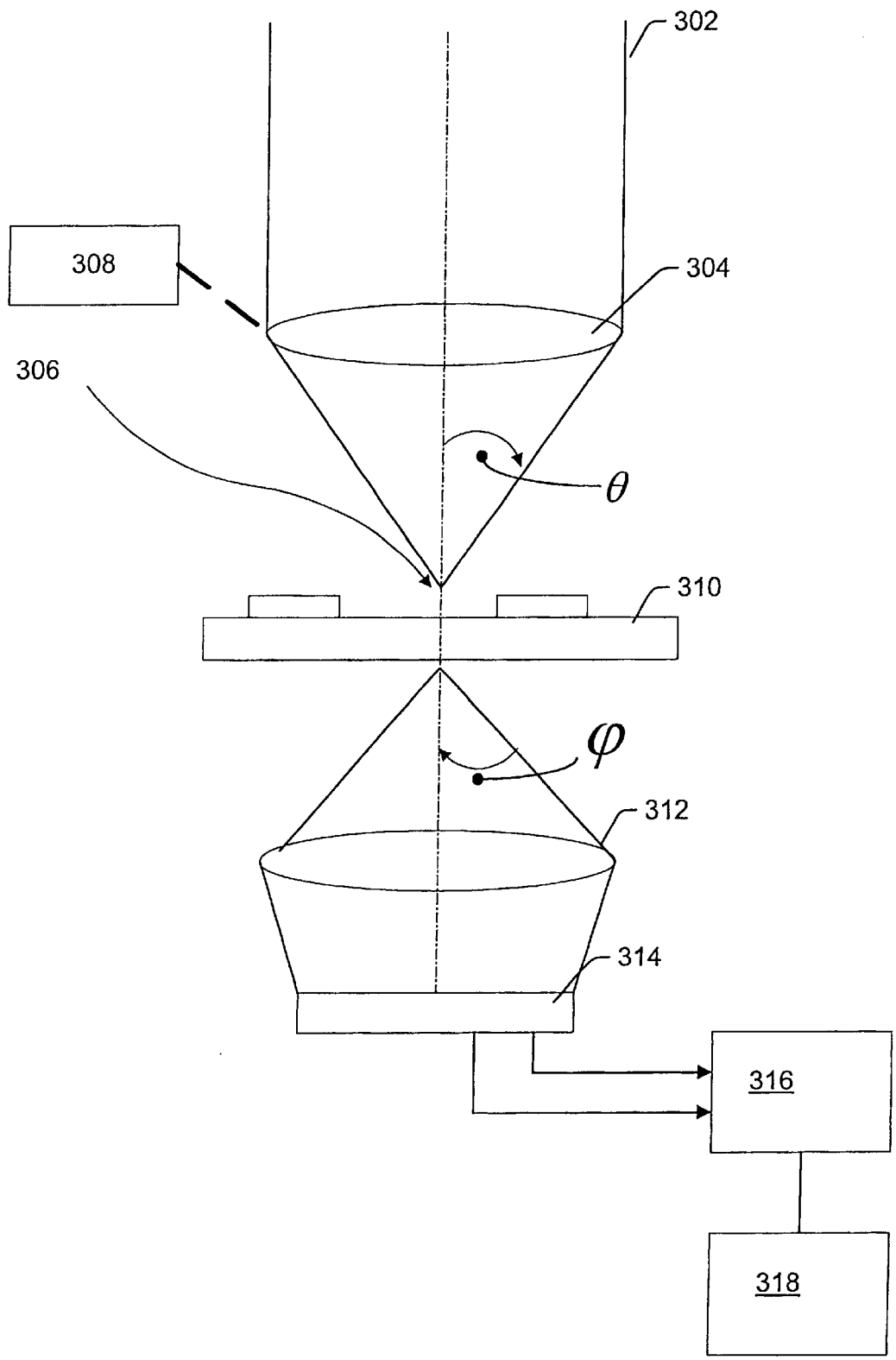
FIG. 3 is a diagram of a scanning optical microscopy system in accordance with one embodiment of the present invention.

A diagram of an optical scanning microscope system employing detection methods of the present invention is shown in FIG. 3. However, the techniques of the present invention may be implemented with any suitably configured detection system, and the system of FIG. 3 is not meant to narrow the scope of the invention. These techniques may be applied to all types of phase shift masks. For example, the techniques described may be applied to alternating phase shift masks, attenuated (tritone) masks, and to binary masks. The incident light inspection beam 302 converges after transmission through objective lens 304 to a focal point 306.

The location of the focal point may be selected through the use of controller 308. One skilled in the art would recognize that various means may be used to control the location of the focal point without departing from the concepts of the invention disclosed herein. For example, a stepper motor could be used to move objective lens 304 in order to locate the focal point 306 at a desired location with respect to mask 310. Moreover, it should be understood that the principles of the present invention may be extended to include manual mechanisms (as well as automatic mechanisms) of selecting the focal point 306. For example, such manual mechanisms of controlling the location of the focal point 306 may include rigidly fastening the objective lens at a desired distance from mask 310 prior to any inspections.

The inspection light beam 302 is shown transmitted through mask 310 to collector 312. Collector 312 collects the light onto a detector 314 over a range of angles. In conventional systems photo detector 314 sums all intensities of light waves received over the full area of the detector. The objective lens angle $\theta$ and the collection angle $\phi$ determine in part the signals generated at the detector. Generally the relationship between the collection angle $\phi$ and the objective lens angle $\theta$ is represented by $\sigma$ (sigma), which, for an air medium, is defined as follows:

$$\sigma = \sin \phi / \sin \theta$$

Conventional optical inspection systems employ relatively wide objective lens angles and collection angles, both typically approximating 45° and resulting in a sigma value approximating 1. However, large sigma values have been shown to wash out signals relating to phase defects. The present invention, in several embodiments, increases the sensitivity to signals related to phase defects by collecting the light waves onto a detector 314 split into regions or zones (e.g., radially symmetric or concentric regions). In practice, it has been observed that higher intensity signals regarding phase defects are produced when the sigma is lower. Sigma values in the range of 0.2 to 0.7 produce suitable results.

Different zones in the detector 314 correspond to different angles or spatial frequency components of the diffracted light being collected. What is meant here by the use of the term signal is the change in detected signal between an object that has a phase defect and an otherwise identical object without the phase defect, i.e. a difference signal between patterns. Signals taken from the outside of the detector experience a reversed sign in comparison to signals taken from an inside portion of the detector. The present invention utilizes the reversed sign of the signal to increase the sensitivity of the apparatus. Experimental results and/or simulations suggest that a detector wired in a differential mode produces a larger signal upon detection of phase defects than a conventionally wired detector. For example, with first and second detector portions equal in area, the intensity of the resulting signal taken in differential mode has been found to be nearly 4 times the intensity of a signal taken in a standard or summing mode from the two detector portions. This results in an increase in the effect of the defect upon an output image, i.e. this technique is more sensitive to defects.

Figure 1A:
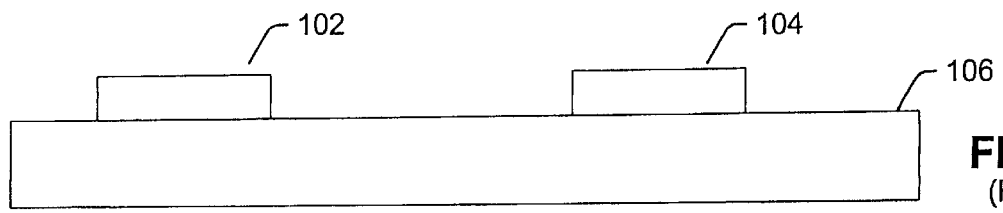
FIGS. 1A and 1B illustrate a conventional chrome on glass photomask.
Figure 1B:
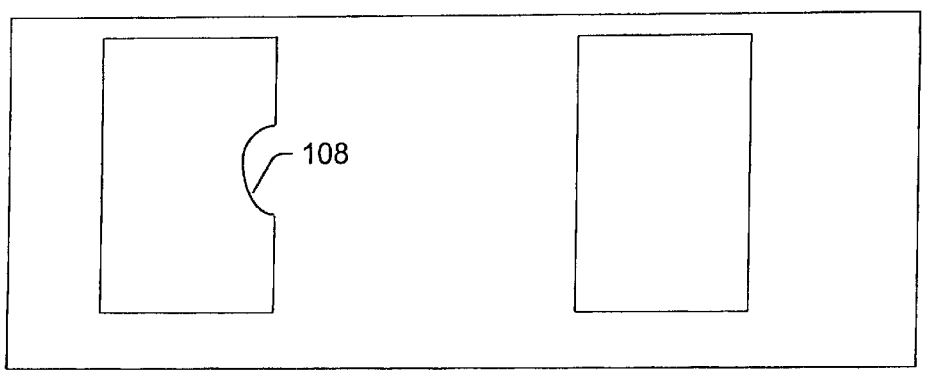

Processing of the separate signals generated by the separate regions or portions of the detector 314 is handled by analyzer 316. In one embodiment, the analyzer 316 comprises a summing amplifier which converts one of the detector signals to its negative value and thus provides a resulting differential signal. In another embodiment, the separate signals from the detector portions are summed to produce a resulting signal equivalent to signals obtained from the full detector using conventional scanning optical microscopy systems to identify defects, such as pattern defects as illustrated by defect 108 in FIG. 1B. Analyzer 316 may comprise a processor with appropriate connective circuitry well known to those of skill in the art or may include a simple summing circuit without a connected processor. Alternatively, the analyzer 316 for analyzing detected signals and the controller 308 for initiating detection may be integrated in a single device comprising any suitable combination of software and hardware. It is to be understood that the invention is not limited in its application to the details of construction or arrangement of analyzing components described or illustrated but extends to all configurations wherein the detector signals may be processed.

Figure 4A:
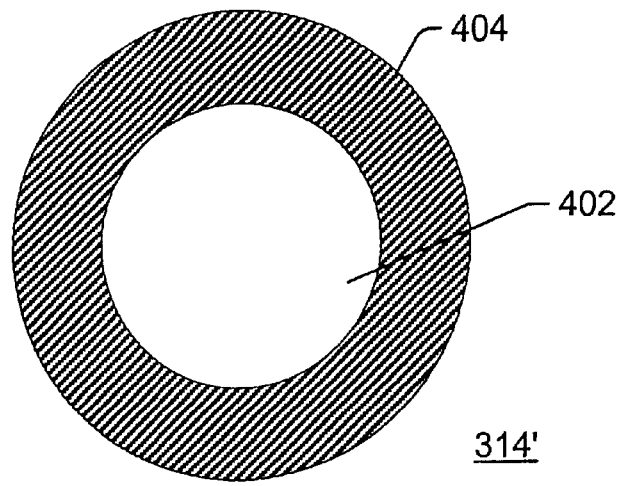
FIGS. 4A, 4B and 4C depict top views of a split detector in accordance with embodiments of the present invention.
Figure 4B:
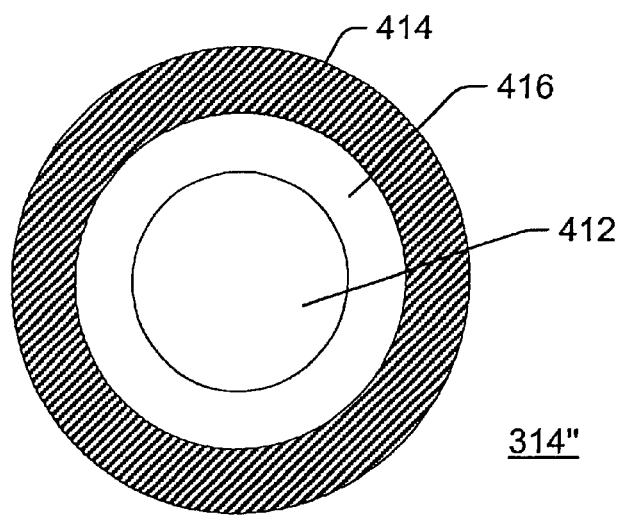

FIGS. 4A and 4B depict top views of a first and second embodiment, respectively, of detector 314. In the first embodiment shown in FIG. 4A the detector 314' is divided into a first portion 402 and a second portion 404. In a specific embodiment, first portion 402 comprises a circular region and second portion 404 comprises a contiguous annular region. The first and second portions are concentric ideally about the centerline of the light waves collected by collector 312. In a specific embodiment, first portion 402 and second portion 404 are equal in area. This may be accomplished, for example, in using the circular and annular portions described by setting the outer diameter of the circular first portion 402 to be equal to about 0.7 times the outer diameter of the annular second portion 404. Each of the portions therefore represents a portion of the detector corresponding to a smaller range of angles, i.e., a lower sigma value.

The embodiments of the present invention achieve improved sensitivity by using a detector split into at least two zones and by combining those signals from the separate zones in a differential manner. Suitable results have been obtained when the detection and the subsequent processing of the signals by the analyzer have been applied to defocused light beams. While not wishing to be bound by any theory, it is believed that the mechanisms involved in producing the larger signal using defocusing are based on the complex amplitudes of the optical field. Phase information imaging is described in greater detail in "Fourier Imaging of Phase Information in Scanning and Conventional Optical Microscopes", C. J. R. Sheppard and T. Wilson, Philosophical Trans. of the Royal Society of London, Vol. 295, A1415, February, 1980, pp. 513–536, which is incorporated fully by reference for all purposes.

In focussed images direct phase information is lost when the detector converts the complex amplitude A of the optical field to an electrical intensity AA. The optical transfer function at focus is real so for all phase shift objects the image intensity at the site of the phase defect is nearly the same as it would be in the case of no phase defect being present. In defocused images the transfer function has an imaginary part. As a result of this out of phase, imaginary part of the focused beam, the contrast of phase defects is greatly increased when defocus is coupled with a low sigma.

Light scattered from most small phase defects is in quadrature to the unscattered light. This is undesirable, as a small signal in quadrature to the unscattered signal will only appear to second order in the detected signal. That is, if epsilon represent the strength of the amplitude scattering of the phase defect normalized to the amplitude of the unscattered plane wave, and the absolute value of epsilon is small compared to 1, then the image modulation due to the defect responds in proportion to epsilon$^2$. Zernike phase plates and defocus are commonly used to improve phase defect visibility by getting the defect signal to add linearly, not in quadrature, to the unscattered signal, so that the defect modulation is proportional to epsilon, rather than epsilon$^2$, and thus produces a higher amplitude signal.

In an alternate embodiment, shown in FIG. 4B, detector 314" is shown with three zones, a first portion 412, a second portion 414, and a third portion 416 separating the first portion 412 from the second portion 414. In this instance, the third portion 416 represents a "dead" band, i.e., an annular isolation region. None of the light detected by this portion is used to generate an output signal. Various diameters of the first, second, and third portions will produce suitable results. For example, a diameter of the first portion 412 of 0.3 times the outer diameter of the second portion 414, and the outer diameter of the third portion 416 equal to 0.8 times the outer diameter of the second portion 414 works well. Outer diameters of the first portion from 0.3 to 0.8, and the second portion having an inner radius from 0.3 to 0.9 work well.

Figure 4C:
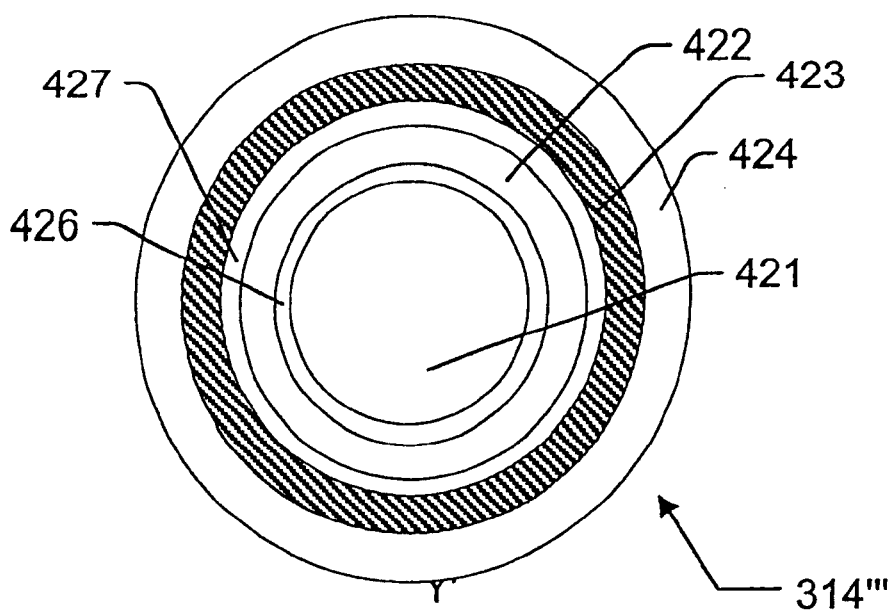

In other embodiments, the detector may comprise any additional number of portions, such as, for example, a third portion and a fourth portion. FIG. 4C depicts a top view of a split detector 314'" having four portions or zones. In one embodiment, the signals generated from a first portion 421 and a third portion 422 may be summed and the signals from a second portion 423 and a fourth portion 424 may also be summed. The resulting summed signals may then be subtracted to provide a difference signal for analysis. In other embodiments, two inner zones (i.e., a selective combination of the detector portions) may be selected from a detector having three or more portions so as to selectively produce a detector signal corresponding to an inspection/collection lens system having a low sigma value. This allows use of a detector which, by virtue of the multiple detector portions, may present different sensitivities for different applications by varying the sigma value. In another embodiment, "active" portions of the detector, i.e., the portions providing a detector signal for further analysis, may be separated by isolation regions (426, 427) or "dead" zones to minimize interference generated in signals in the active portions of the detector. Though in some cases the isolation regions may approximate the active regions in size, the invention is not so limited. The size of the isolation regions may be minimized or in some embodiments the isolation regions may be eliminated and still be within the scope of the present invention. The present invention is not limited to using all of the available zones in the detector to generate a signal, and, as illustrated above, is not limited to selecting contiguous zones for generation of a summed signal. Specific zones or portions may be "dead" zones and the zones selected for summing may be contiguous or not, selected in accordance with the sensitivity desired.

Another advantage to having multiple annular detector segments is that it allows for flexible operation with different pixels sizes. For instance, larger pixels are used at times for mask inspection. This is accomplished by reducing the NA of the objective lens. Since the sigma of the imaging system is given by the ratio of the sine of the collection angle to the sine of NA, changing NA for different pixel sizes requires changing the sine of the collection angle if sigma is to remain the same. If sigma were allowed to increase, as it would if the NA were reduced and no change were made in the detector configuration, the microscope's phase sensitivity would decrease. One way to do this is to have a detector with multiple annular regions so that when the NA is reduced elements closer to the center can be used, thus keeping sigma constant with varying pixel size.

In another embodiment, a Zernike phase shift plate or similar phase plate is introduced in the pupil plane to improve phase sensitivity in lieu of defocusing. Zernike techniques provide a mechanism for emphasizing small phase steps.

Figure 5:
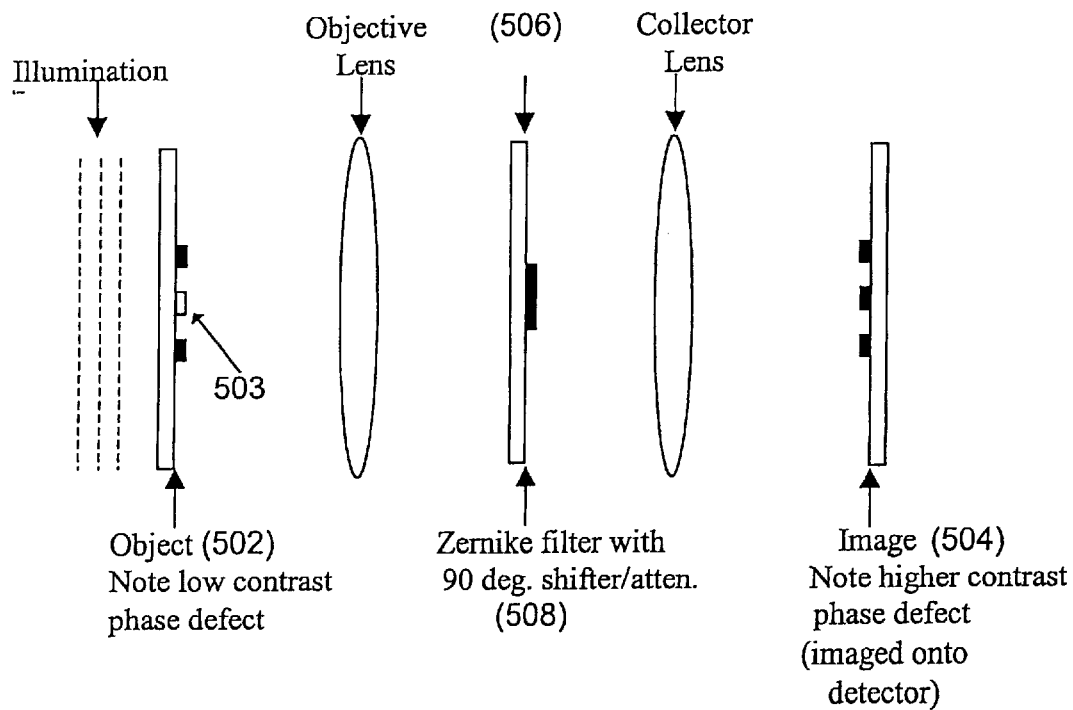
FIG. 5 is a diagrammatic representation of a conventional optical microscopy system utilizing a Zernike plate.

At the left of FIG. 5 an object 502 having a low contrast phase defect 503 is illuminated, and at the right a phase contrast image 504 of this object is produced. The phase contrast image 504 is produced by forming an intermediate Fourier plane 506 of the image and inserting a Zernike phase contrast filter 508 in this plane. This filter 508 shifts the amplitudes of the low spatial frequency components of the image 504, which forms the background of the image 504, by 90 degrees. It may also attenuate the low spatial frequency components of the image 504 as well, which has the effect of reducing the overall brightness of the image but increasing the contrast of phase defects in the image, which is sometimes desirable. The phase contrast is increased by this filter 508 because when the output image is formed from this filtered Fourier plane 506 the background is now collinear in amplitude with the components of the image due to the phase defect. Therefore the signals add linearly rather than in quadrature. For instance, a small phase defect that is 0.1 of the amplitude of the background that is imaged using a phase contrast technique would give an approximately 10% modulation of the image at the point of the defect. However, if this amplitude were in quadrature rather than in phase it would only give approximately a 1% modulation of the image, which would make it much harder to detect.

A defocused imaging system is somewhat like a focused system with a (Zernike) phase plate where the phase shift increases quadratically with spatial frequency (or pupil radius). A Zernike plate or a complex amplitude plate may be used to produce a phase shift between the regions of the detector, such as between the annular and central regions. Zernike plates usually specify a 90 degree phase shift and usually are attenuating for the direct light (or zero order). Those skilled in the art with the benefit of this specification would recognize that complex amplitude plates may be selected to produce variations in both phase and amplitude to meet a desired sensitivity.

Typically, the signals generated from the analyzer are connected to a display generator 318 (see FIG. 3) in order to create a display of the inspected mask. The display generator may comprise a CRT, an LCD screen, or other suitable display device coupled with appropriate processing circuitry to convert the resulting voltage signals received as the light beam scans the mask to an image on the display screen of the display generator 318. Generally, a phase defect image derived from an inspected mask will show edges of layers in addition to phase defects. For example, a difference image may be obtained from two identical areas of the mask to isolate the images generated by the phase defects. If the difference image contains pixel values above a certain threshold, then a defect has been identified. This threshold is set so that defects above a certain specified size are found reliably, while the number of false and/or nuisance defects is kept acceptably low.

In one embodiment, the techniques of the present invention permit pattern defect inspections and phase shift inspections to proceed using a single scanning optical microscopy system in two passes. The number of passes depends on the algorithms, noise, and desired defect sensitivities.

Figure 6:
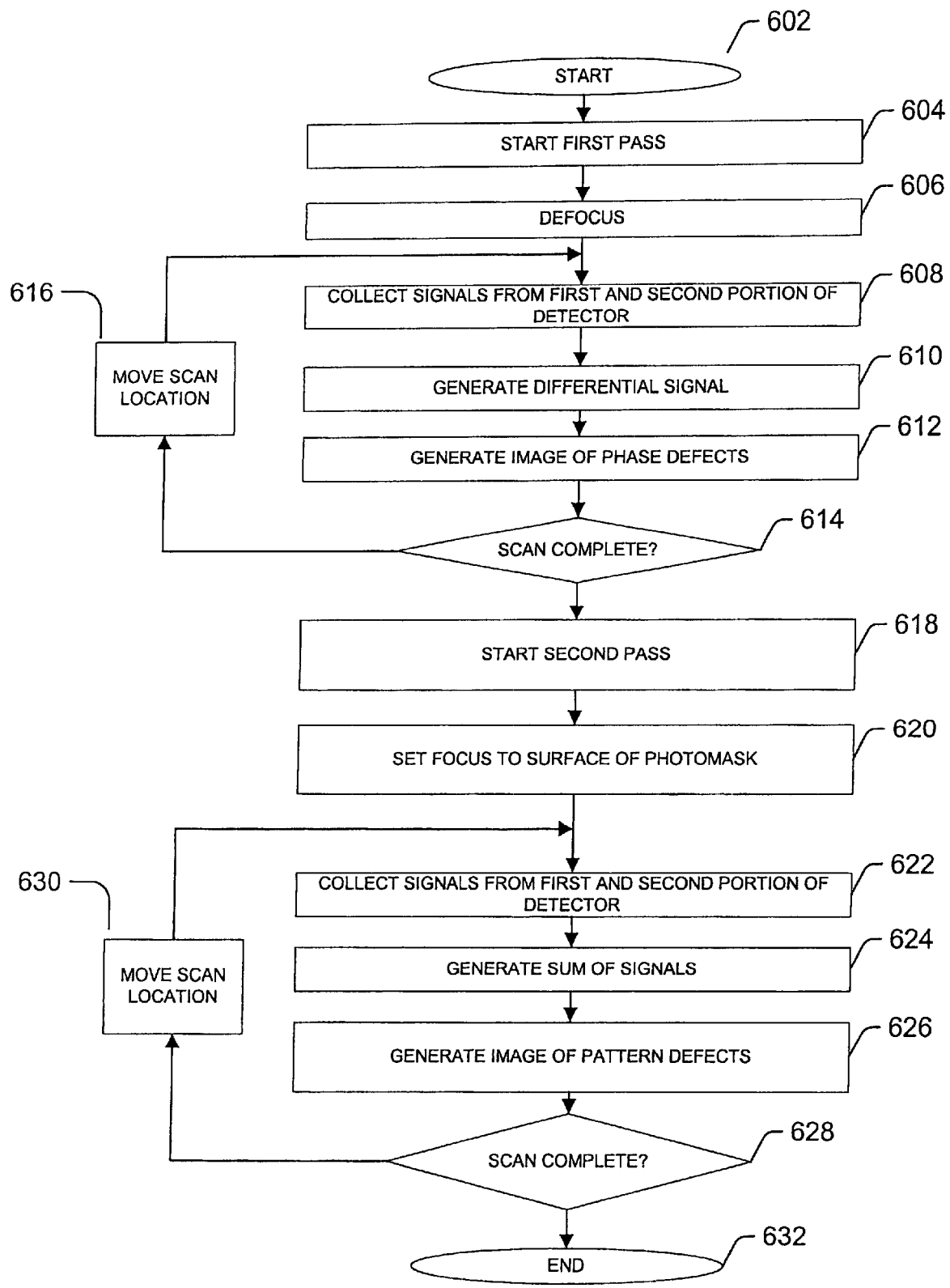
FIG. 6 is a flowchart illustrating a procedure for inspecting phase shift defects and pattern defects in accordance with one embodiment of the present invention.

FIG. 6 is a flowchart illustrating an inspection technique for phase shift defects and for pattern defects in accordance with one embodiment of the present invention. In general terms, the system completes pattern and phase defect inspections in two passes over the photomask to be inspected. The first pass commences with an inspection for phase defects in the photomask (604). Phase defect inspection, in accordance with several embodiments, requires a defocused image. The focus is set to a predetermined distance in one direction from the surface of the photomask (606). Suitable distances will vary as a function of the wavelength (lambda) of the impinging light waves and numerical aperture (NA) of the objective lens, specifically in proportion to lambda/$NA^2$. For example, a suitable range lies from a distance 0.5 to 3*lambda/$NA^2$. Suitable results have been obtained in the range from about 200 nm to about 500 nm but these values may vary according to the factors as discussed above. The scan commences with the incident light directed to a spot on the photomask and the collection of the resulting signals from a first and second portion of the detector (608). In this first mode, a differential signal is generated from separate portions of the detector (610). Subsequently, the resulting signal is used to generate an image of the mask to identify defects (612). A bright or dark picture element will be generated to correspond to the scanned spot. If the scan of the photomask is not complete (614), the scanning continues over the next section of the photomask (616). Various mechanisms may be used to perform the scanning as is known to those of skill in the art. For example, in one embodiment, the light is focused on a spot followed by the generation of detector signals. In order to perform the two-dimensional scan, the photomask may be moved in one direction and the beam moved in a direction perpendicular to the mask movement.

Once the scanning of the photomask for phase defects is complete, the second pass commences (618). Initially, in this conventional inspection mode, the focus is set to the surface of the photomask (620). This location is in fact typically set to the surface of the chrome layers patterned on top of the quartz layer of the photomask. In this mode, the signals are collected from the full detector by generating the sum of signals from the separate portions of the detector (622 and 624). As with the case of the phase defect inspection, the resulting signal is used to generate a picture element of an image displaying pattern defects (626). Scanning of the mask continues for pattern defects if the image is not complete (628, 630). Although this embodiment is shown commencing with an inspection for phase defects in a first mode followed by an inspection for pattern defects in a second mode, it will be recognized by those skilled in the art that the order of inspections may easily be interchanged without departing from the basic principles of the invention.

Although the foregoing invention has been described in some detail for purposes of clarity of understanding, it will be apparent that certain changes and modifications may be practiced within the scope of the appended claims. It should be noted that there are many alternative ways of implementing both the method and apparatus of the present invention. Accordingly, the present embodiments are to be considered as illustrative and not restrictive, and the invention is not to be limited to the details given herein, but may be modified within the scope and equivalents of the appended claims.

What is claimed is:

1. A method for detecting phase defects in a semiconductor processing photomask, the method comprising:
    setting a focus of an optical inspection beam to a predetermined distance above or below a surface of semiconductor processing photomask,
    collecting light reflected from or transmitted through the semiconductor processing photomask at a detector comprising at least two portions,
    generating a first signal from a first portion of the at least two portions and a second signal from a second portion of the at least two portions, and
    obtaining the difference between the first signal and the second signal to produce a resulting signal indicating whether there is a defect present.

2. The method recited in claim 1 wherein the predetermined distance above or below the surface of the semiconductor processing photomask is selected so that the optical inspection beam is defocused.

3. The method recited in claim 1 wherein the first portion comprises a circular region and the second portion comprises an annular region outside the first portion and wherein both portions are concentric.

4. The method recited in claim 3 wherein the first and second portions are separated by a third portion which is annular in shape and concentric with the first and second portions.

5. The method recited in claim 3 wherein the diameter of the first portion is approximately 0.7 times the outer diameter of the second portion.

6. The method recited in claim 3 wherein the diameter of the first portion is approximately 0.3 times the outer diameter of the second portion and the inner diameter of the second portion is approximately 0.8 times the outer diameter of the second portion.

7. The method recited in claim 3 wherein the detector further comprises a third portion and a fourth portion and further comprising
    generating the first signal from the first portion and the third portion and the second signal from the second portion and the fourth portion.

8. The method recited in claim 7 wherein each of the third and fourth portions are annular regions and wherein the third portion is positioned between the first and second portions and the fourth portion is positioned outside the second portion.

9. The method recited in claim 7 wherein the first portion and the third portion are not contiguous.

10. The method recited in claim 7 wherein the first portion and the third portion are separated by an annular isolation region.

11. The method recited in claim 7 wherein at least two of the first, second, third, and fourth portions are separated by annular shaped isolation regions.

12. The method recited in claim 7 wherein the first portion and the third portion are contiguous.

13. The method recited in claim 1 wherein the first portion and the second portion are approximately equal in area.

14. The method recited in claim 1 wherein the predetermined distance lies in the range of 200 to 500 nm.

15. The method recited in claim 1 wherein the predetermined distance lies in the range of 0.5 to 3 times a wavelength of the optical inspection beam divided by the square of the numerical aperture of an objective lens used to diffract the optical inspection beam directed towards the photomask.

16. The method recited in claim 1 wherein the setting a focus and collecting light reflected from or transmitted through a semiconductor processing photomask is performed using a combination of objective lens and collection lens producing a sigma value from about 0.2 to about 0.7.

17. The method recited in claim 1 wherein the resulting signal is used to generate an image.

18. The method for detecting phase defects in a semiconductor processing photomask in a first mode recited in claim 1, the method further comprising in a second mode:
    setting a focus of an optical inspection beam to a surface of the semiconductor processing photomask,
    collecting light reflected from or transmitted through the semiconductor processing photomask at a detector comprising a first portion and a second portion, wherein each of the first and second portions generates a signal, and combining by addition the signal from the first portion and the signal from the second portion of the detector to produce an image of the semiconductor processing photomask.

19. A method for detecting phase defects in a semiconductor processing photomask, the method comprising:

setting a focus of an optical inspection beam of an inspection system having an objective lens and a collection lens to a predetermined distance above or below a surface of semiconductor processing photomask, collecting light reflected from or transmitted through the semiconductor processing photomask at a detector comprising a plurality of portions, wherein the collection lens, objective lens, and detector configuration are related by a sigma value, generating a first signal from at least a first portion, alone or in combination with one or more of the plurality of portions, and a second signal from at least a second portion of the plurality of portions, one of the plurality of portions being circular in shape and the remaining portions of the plurality having annular shapes and obtaining the difference between the first signal and the second signal to produce a resulting signal indicating whether there is a defect present.

20. The method recited in claim 19 wherein the first signal and the second signal are generated from portions of the plurality of detector portions selected to correspond to a predetermined sigma value.

21. The method recited in claim 19 wherein the portions of the plurality of detector portions selected for generation of the first and second signals are selected to compensate for changes in the objective lens used in the system.

22. The method recited in claim 21 wherein portions of the plurality of detector portions are selected near the center of the detector to compensate for a reduced NA of the objective lens.

23. A method for detecting phase defects in a semiconductor processing photomask, the method comprising:

producing an image using a Zernike phase shift plate on an inspection light beam directed to a semiconductor processing photomask, collecting light reflected from or transmitted through the semiconductor processing photomask at a detector comprising a first portion and a second portion, wherein each of the first and second portions generates a signal, and obtaining the difference between the signal from the first portion and the signal from the second portion of the detector to produce a resulting signal indicating whether there is a defect present.

24. The method recited in claim 23 wherein the first portion comprises a circular region and the second portion comprises an annular region outside the first portion and wherein both portions are concentric.

25. The method recited in claim 24 wherein the first and second portions are separated by a third portion which is annular in shape and concentric with the first and second portions.

26. The method recited in claim 23 wherein the first portion and the second portion are approximately equal in area.

27. The method recited in claim 24 wherein the diameter of the first portion is approximately 0.7 times the outer diameter of the second portion.

28. The method recited in claim 25 wherein the diameter of the first portion is approximately 0.3 times the outer diameter of the second portion and the inner diameter of the second portion is approximately 0.8 times the outer diameter of the second portion.

29. The method recited in claim 23 wherein the resulting signal is used to generate an image.

30. A scanning optical microscopy system configured to detect phase defects in a semiconductor processing photomask comprising:

an optical beam generator to direct a light beam towards a surface of the semiconductor processing mask;

a detector comprising a first portion and a second portion, each of the first portion and the second portion generating a signal from light collected from a semiconductor processing photomask;

a controller for setting a focus of the light beam to a predetermined distance above or below the surface of the semiconductor processing photomask; and an analyzer configured to obtain the differences in the signals from the first portion and the second portion of the detector.

31. The scanning optical microscopy system recited in claim 30 wherein the first portion comprises a circular region and the second portion comprises an annular region outside the first portion and wherein both portions are concentric.

32. The scanning optical microscopy system recited in claim 30 wherein the first and second portions are separated by a third portion which is annular in shape and concentric with the first and second portions.

33. The scanning optical microscopy system recited in claim 30 wherein the first portion and the second portion are approximately equal in area.

34. The scanning optical microscopy system recited in claim 31 wherein the diameter of the first portion is approximately 0.7 times the outer diameter of the second portion.

35. The scanning optical microscopy system recited in claim 31 wherein the diameter of the first portion is approximately 0.3 times the outer diameter of the second portion and the inner diameter of the second portion is approximately 0.8 times the outer diameter of the second portion.

36. The scanning optical microscopy system recited in claim 31 further comprising an image generator for using the resulting signal to generate an image.

37. The scanning optical microscopy system recited in claim 30 wherein the controller is further configured for setting the focus of the light beam to a surface of the semiconductor processing photomask and wherein the analyzer is further configured to selectively obtain the sum of the signals from the first portion and the second portion of the detector.

38. A scanning optical microscopy system configured to detect phase defects in a semiconductor processing photomask comprising:

an optical beam generator to direct a light beam towards a surface of the semiconductor processing mask;

a detector comprising a first portion and a second portion, each of the first portion and the second portion generating a signal from light collected from a semiconductor processing photomask;

a complex amplitude plate located on the incident plane to generate a defocused image; and an analyzer configured to obtain the differences in the signals from the first portion and the second portion of the detector.

39. The system recited in claim 38 wherein the complex amplitude plate is a Zernike plate.

* * * * *